US00PP22199P2

(12) United States Plant Patent
Dirr

(10) Patent No.: US PP22,199 P2
(45) Date of Patent: Oct. 18, 2011

(54) CRAPEMYRTLE PLANT NAMED 'GAMAD VII'

(50) Latin Name: ***Lagerstroemia* hybrid**
Varietal Denomination: Gamad VII

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 12/800,577

(22) Filed: May 18, 2010

(51) Int. Cl.
*A01H 5/00* (2006.01)

(52) U.S. Cl. ..... Plt./252
(58) Field of Classification Search ..... Plt./252
See application file for complete search history.

(56) References Cited

U.S. PATENT DOCUMENTS

PP17,411 P2 2/2007 Dirr

*Primary Examiner* — Annette Para
(74) *Attorney, Agent, or Firm* — Davis Wright Tremaine LLP

(57) ABSTRACT

A new and distinct cultivar of crapemyrtle, 'Gamad VII' is provided. 'Gamad VII' is a *Lagerstroemia indica*×*Lagerstroemia fauriei*, which is characterized by compact growth habit, high *Cercospora* resistance, and early July flowering with abundant true pink flowers.

2 Drawing Sheets

Latin name of the genus and species of the plant claimed: 'Gamad VII' is a crapemyrtle plant that is a *Lagerstroemia* hybrid.

Variety denomination: The new crapemyrtle plant claimed is of the variety denominated 'Gamad VII'.

BACKGROUND OF THE INVENTION

The present invention relates to the discovery of a new and distinct cultivar of the ornamental flowering shrub *Lagerstroemia indica*×*Lagerstroemia fauriei*, commonly known as crapemyrtle, and herein referred to by the varietal denomination 'Gamad VII', as herein described and illustrated.

The new crapemyrtle plant variety 'Gamad VII' originated from open-pollinated seed of 'Pocomoke' (unpatented), a compact, rose-pink flowered introduction in 1999 from the United States National Arboretum (USDA). 'Gamad VII' was derived from plants grown in 2001 at Athens, Ga. from seed collected from open pollinated 'Pocomoke' plants. The seedlings were planted in containers at Dearing, Ga. and selected on the basis of the following criteria: 1) compact habit; 2) mildew resistance; 3) early flowering; and 4) flower color and quality. The new variety, 'Gamad VII', was selected in 2003 at Dearing, Ga.

Asexual reproduction by traditional vegetative cuttings since 2003 at Dearing, Ga. has shown that the distinguishing characteristics of this new crapemyrtle variety, 'Gamad VII', are stable and reproduce true-to-type in successive generations.

SUMMARY OF THE INVENTION

The new crapemyrtle plant variety 'Gamad VII' has not been observed under all possible environmental conditions. The phenotype may vary somewhat with variations in environment and cultural practices such as temperature and light intensity without, however, any variance in genotype.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following traits have been repeatedly observed in Dearing, Ga., and are determined to be the unique characteristics of the new crapemyrtle plant variety 'Gamad VII':

1. Compact growth habit
2. High *Cercospora* resistance
3. Early July flowering with abundant deep red-purple flowers The new variety 'Gamad VII' can be compared to 'Gamad V' (U.S. Plant Pat. No. 17,411), a compact pink flowering variety. 'Gamad VII' is slightly larger than 'Gamad V', with a looser, finer textured structure.

'Gamad VII' can also be compared to 'Pocomoke'. 'Gamad VII' possesses greater fungal resistance relative to 'Pocomoke'. The flowers of 'Gamad VII' are more abundant than 'Pocomoke' and are pink (Red-purple 68B) whereas the flowers of 'Pocomoke' are bubble-gum pink (Red-purple 73B, fading to Violet 84B).

BRIEF DESCRIPTION OF THE DRAWINGS

The accompanying photographic illustrations show typical specimens in full color of the foliage and fruit of the new variety 'Gamad VII'. The colors are as nearly true as is reasonably possible in a color representation of this type.

BOTANICAL DESCRIPTION

Figure 1:
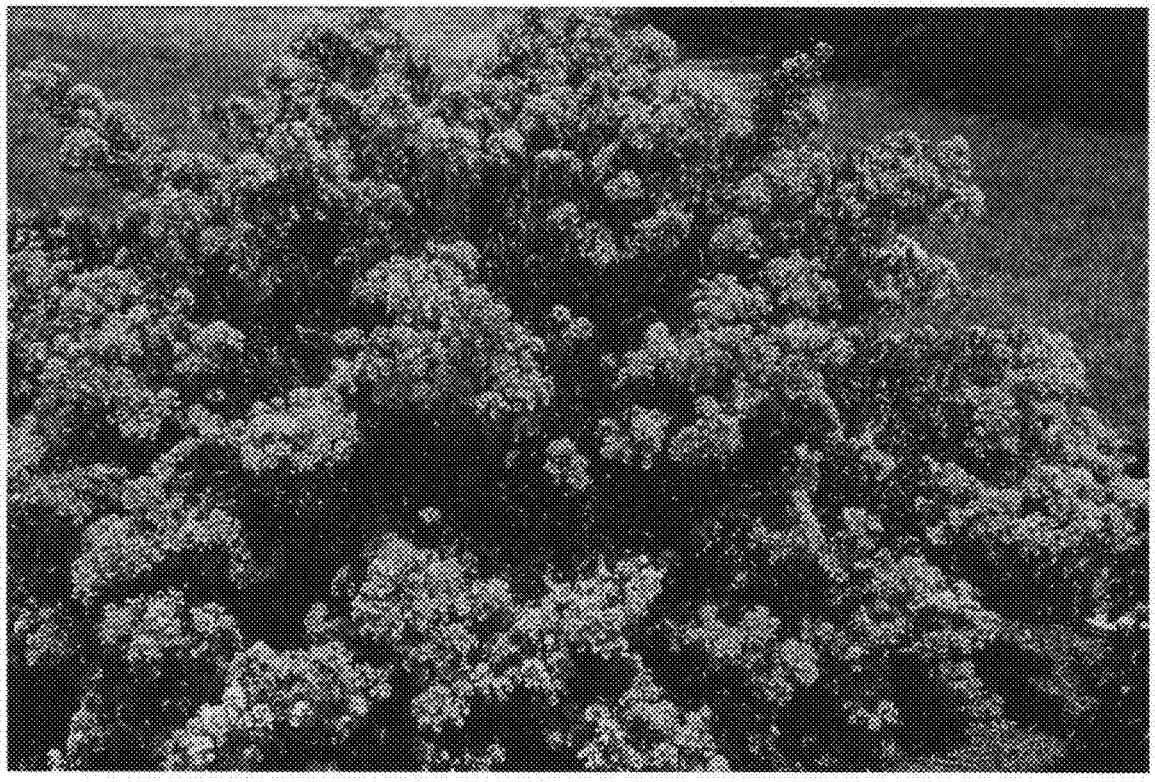
FIG. 1 is a photograph of the new variety 'Gamad VII'.
Figure 2:
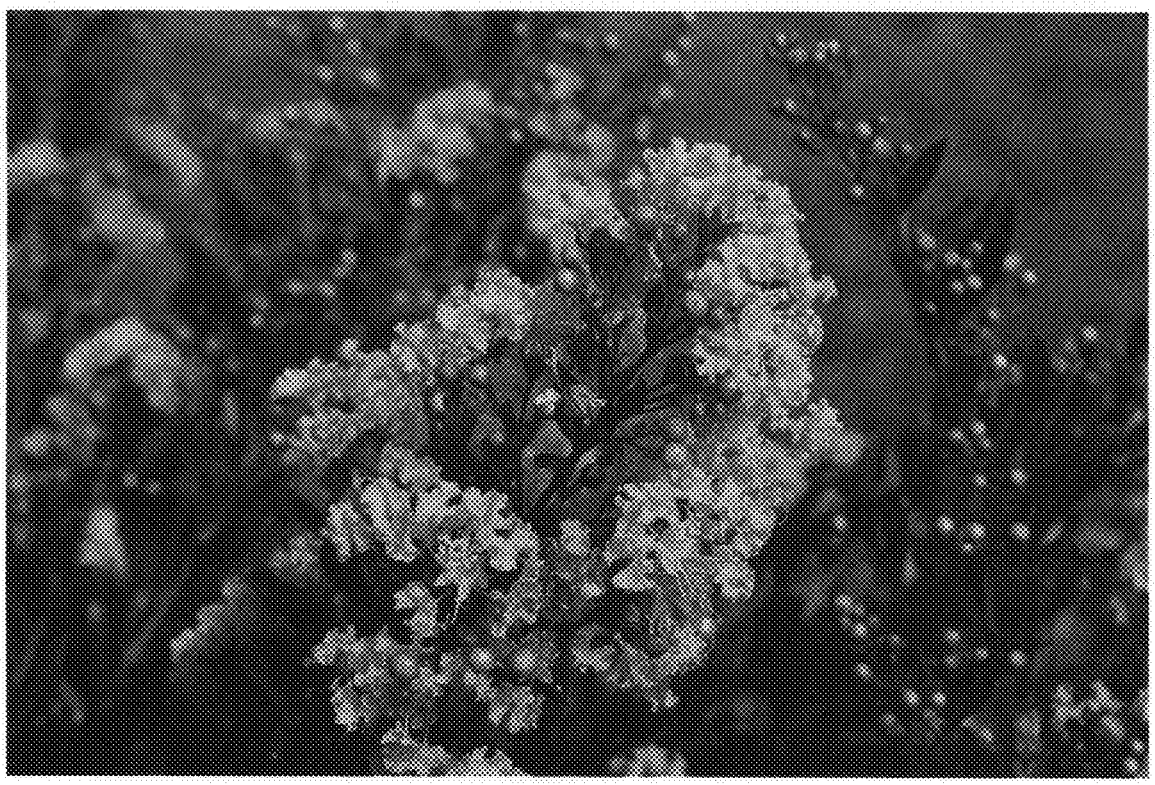
FIG. 2 is a photograph of the fruit and flowers of the new variety 'Gamad VII'.

The following is a detailed description of the botanical and pomological characteristics of the new variety 'Gamad VII'. Where dimensions, sizes, colors, and other characteristics are given, it is to be understood that such characteristics are approximations and averages set forth as accurately as practicable. The descriptions reported herein are largely from specimen plants potted in June 2005 at Dearing, Ga. Data was obtained in August 2006 on plants that were 9 years old.

PLANT

Habit: Upright, rounded.
Size:
*Height.*—Approximately 97 cm (measured at highest point).
*Width.*—Approximately 142 cm (measured at widest point).
Texture: Medium.

STEMS

Color: About Greyed-brown RHS N199B in first year, changing to about Greyed-brown RHS N199C in second year.
Diameter: Approximately 2 mm in first year, growing to about 4 mm in second year.
Pubescence: None.
Exfoliation: Wing-like ridges (somewhat corky) in first year; none in second year.
Shape: Square.
Pith:
*Type.*—Solid.
*Diameter.*—Approximately 2 mm.
*Color.*—About Green RHS 138B.
Odor (of bruised stem): None.
Lenticels: None.
Internode length: Approximately 10 mm.

VEGETATIVE BUDS

Arrangement: Sub-opposite.
Type: Three-scaled, conical.
Size:
*Length.*—Approximately 2 mm.
*Width.*—Approximately 1 mm.
Scale number: Approximately 3.
Scale color:
*Center scale.*—About Yellow-green RHS N144D.
*Outside scales.*—About Grey-Brown RHS N199D.
Position/disposition: Flat against stem.
Number at node: Single buds, approximately 2.
Pubescence: Finely hairy.
Shape: Ovoid.

LEAF SCAR

Shape: Raised half ellipse
Vascular bundle traces: None observed.
Pubescence: None.
Position of bud: Directly on top.
Color differentiation: About Yellow-green RHS 144A at abscission, otherwise about Brown RHS N200A.
Size:
*Height.*—Approximately 1 mm.
*Width.*—Approximately 1 mm.

TRUNK OR LARGE STEMS

Color: About Grey-brown RHS N199A.
Size of stem on which exfoliation begins: None visible yet.
Diameter: Approximately 15 mm.
Texture: Rough.

LEAF

Color at emergence:
*Upper.*—About Greyed-orange RHS176B.
*Lower.*—About Greyed-orange RHS 176B.
Color during summer season:
*Upper.*—About Green RHS 139A.
*Lower.*—About Green RHS 137C.
Color during fall season:
*Upper.*—Range of colors covering from about Yellow-orange RHS 21A to about Orange-red RHS 34A to about Red RHS 46A.
*Lower.*—About Yellow-orange RHS 22A.
Mature size:
*Length.*—Approximately 45.7 mm (on average).
*Width.*—Approximately 17.6 mm (on average).
Apex: Acuminate.
Base: Cuneate.
Margin: Entire, undulating.
Shape: Privet-shaped, cupped (elliptical).
Vein color: About Yellow-green RHS 147B.
Pubescence: Few hairs along leaf margin, otherwise none observed.
Arrangement on stem: Sub-opposite.
Venation: Pinnate.
Texture: Leathery
*Thickness.*—Medium thickness.
*Degree of waxiness of surfaces.*—Smooth, not waxy.

PETIOLE

Length: Approximately 2.7 mm (on average).
Shape: Oval-rounded to rounded.
Color: About Yellow-green RHS 146C.
Pubescence: None.
Diameter: Approximately 1 mm.

FLOWER BUDS

Size:
*Length.*—Approximately 6 mm.
*Width.*—Approximately 6 mm.
Color: About Greyed-red RHS 178B at maturity, about Yellow-green RHS 145A at emergence.
Shape: Rounded.
Pubescence: Very finely hairy.
Time of full maturity: July.
Time range for showiness: Approximately 8 to 10 weeks.

FLOWER

Inflorescences:
*Type.*—Paniculate.
*Size.*—Length: 12 to 15 cm. Width: 8 to 10 cm.
*Color at emergence.*—About Red-purple RHS 68B.
*Color at full bloom.*—About Red-purple RHS 68B.
*Color at fading.*—Red-purple 68B.
*Peduncle.*—Color: About Greyed-orange RHS 176B. Pubescence: None.
*Number of individual flowers per inflorescence.*—25 to 35.
Petals:
*Size.*—Length: Approximately 18.8 mm (on average). Width: Approximately 13.2 mm (on average).
*Shape.*—Fan-shaped.
*Apex.*—Rounded.

*Base.*—Auriculate.
*Margin.*—Ruffled.
*Pubescence.*—None.
*Texture.*—Smooth.
*Color at peak of bloom.*—Upper surface: About Red-purple RHS 68B. Lower surface: About Red-purple RHS 68BA.
*Pedicels.*—Color: About Greyed red RHS 181A. Pubescence: None. Length: Approximately 8 mm to 10 mm.

MALE REPRODUCTIVE STRUCTURES

Number: Approximately 6 (fertile); approximately 20 to 30 (sterile).
Pollen color: About Yellow RHS 13B.
Pubescence: None.
Anther:
*Size.*—(Both fertile and sterile plants). Length: Approximately 2 mm. Width: Approximately 1 mm.
*Color.*—About Greyed-orange RHS 165B (fertile); about Yellow-orange RHS 20A (sterile).
Filament:
*Size.*—Approximately 15 mm (fertile); approximately 8 mm to 10 mm (sterile).
*Color.*—About Red-purple RHS 68B (fertile); about Red-purple RHS 65B (sterile).

FEMALE REPRODUCTIVE STRUCTURES

Pistil:
*Size.*—Length: Approximately 20 mm. Width: Approximately 0.5 mm.
*Position.*—Superior.
*Pubescence.*—None.
Stigma:
*Shape.*—Oval.
*Color.*—About Yellow-green RHS 147B.
*Pubescence.*—None.
Style:
*Length.*—Approximately 2 cm.
*Shape.*—Linear.
*Color.*—About Red RHS 48A.
*Pubescence.*—None.
Ovary:
*Shape.*—Round.
*Number.*—Approximately 1 per flower.
*Pubescence.*—None.
*Size (diameter).*—Approximately 2 mm.
*Color.*—About Yellow RHS 2B.

FRUIT

Type: Capsule.
Size:
*Length.*—Approximately 1 cm to 1.5 cm.
*Width.*—Approximately 8 mm.
Color during ripening:
*Early.*—About Yellow-green RHS 144A.
*Late.*—About Greyed-purple N186A.
Shape: Round.
Number per infructescence: Approximately 20 to 30.
Pubescence: None.
Persistence (effective period): Approximately 3 months.

SEED

Shape: Oval-rounded.
Size:
*Length.*—Approximately 8 mm.
*Width.*—Approximately 3 mm.
Color: About Brown RHS 200 C (seed); about Greyed-brown RHS 199A (wing).
Number per fruit: Approximately 30 to 35.
Pubescence: None.

What is claimed is:

1. A new and distinct variety of crapemyrtle plant named 'Gamad VII', substantially as illustrated and described herein.

* * * * *